United States Patent
Prior et al.

(10) Patent No.: US 6,464,882 B1
(45) Date of Patent: Oct. 15, 2002

(54) ANNULAR CHROMATOGRAPH

(75) Inventors: Adalbert Prior, Götzis; Jürgen Wolfgang, Bregenz, both of (AT)

(73) Assignee: Prior Separation Technology GmbH, Gotzis (AT)

(*) Notice: Subject to any disclaimer, the term of this patent is extended or adjusted under 35 U.S.C. 154(b) by 0 days.

(21) Appl. No.: 09/646,056

(22) PCT Filed: Mar. 19, 1999

(86) PCT No.: PCT/AT99/00075
§ 371 (c)(1), (2), (4) Date: Oct. 20, 2000

(87) PCT Pub. No.: WO99/47913
PCT Pub. Date: Sep. 23, 1999

(30) Foreign Application Priority Data

Mar. 19, 1998 (AT) .............................. 170/98 U

(51) Int. Cl.⁷ .............................. B01D 15/08
(52) U.S. Cl. .................. 210/657; 210/656; 210/659; 210/198.2
(58) Field of Search .............. 95/82; 96/105; 210/635, 636, 657, 659, 198.2

(56) References Cited

U.S. PATENT DOCUMENTS

| | | | |
|---|---|---|---|
| 3,077,103 A | 2/1963 | Heaton | 73/23 |
| 3,666,105 A | * 5/1972 | Fox | 210/198.2 |
| 3,732,982 A | * 5/1973 | Dunnill | 210/198.2 |
| 5,124,023 A | * 6/1992 | Bosserman | 210/657 |
| 5,149,436 A | 9/1992 | Taniguchi et al. | 210/657 |
| 5,217,608 A | 6/1993 | Conway | 210/198.2 |

FOREIGN PATENT DOCUMENTS

| | | | |
|---|---|---|---|
| EP | 0 328 146 | 8/1989 | 210/198.2 |
| JP | 6-204048 | 7/1994 | 210/198.2 |

OTHER PUBLICATIONS

Abstract of Japan Patent No 6–204048 Jul. 22, 1994.

* cited by examiner

Primary Examiner—Ernest G. Therkorn
(74) Attorney, Agent, or Firm—Oliff & Berridge, PLC

(57) ABSTRACT

The invention related to an annular chromatograph including a particle bed which rotates on a rotary plate (3), said plate having eluate drainage lines, with regard to a stationary base and a stationary feeder head (10) with continuous feeder lines. The annular chromatograph has a central column (2) provided on a rotary plate and extending upwards through the feeder head. A tightening device (16,17) for pressing the feeder head (10) on the cylinder sleeve (6) is arranged on said column.

15 Claims, 2 Drawing Sheets

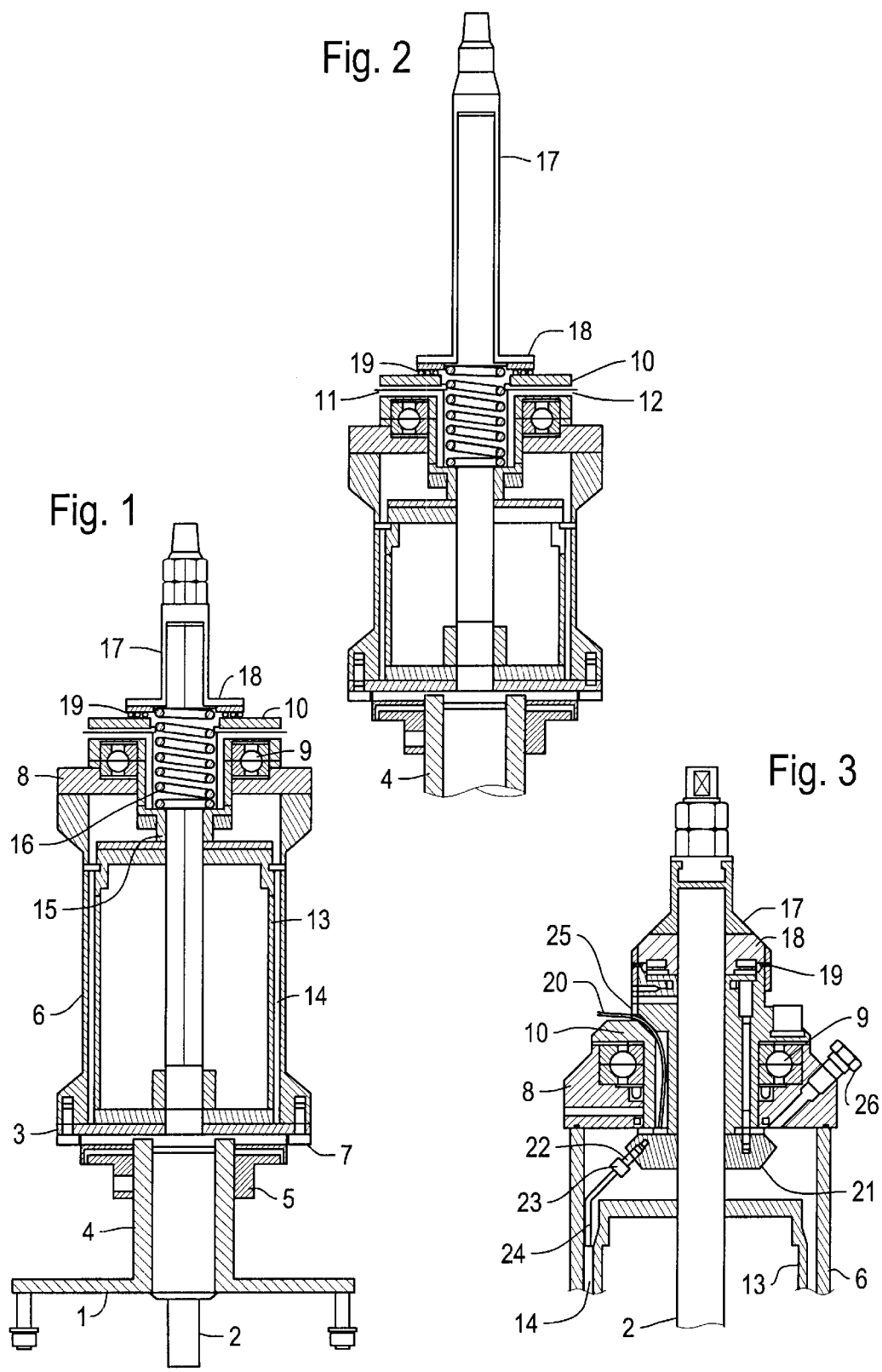

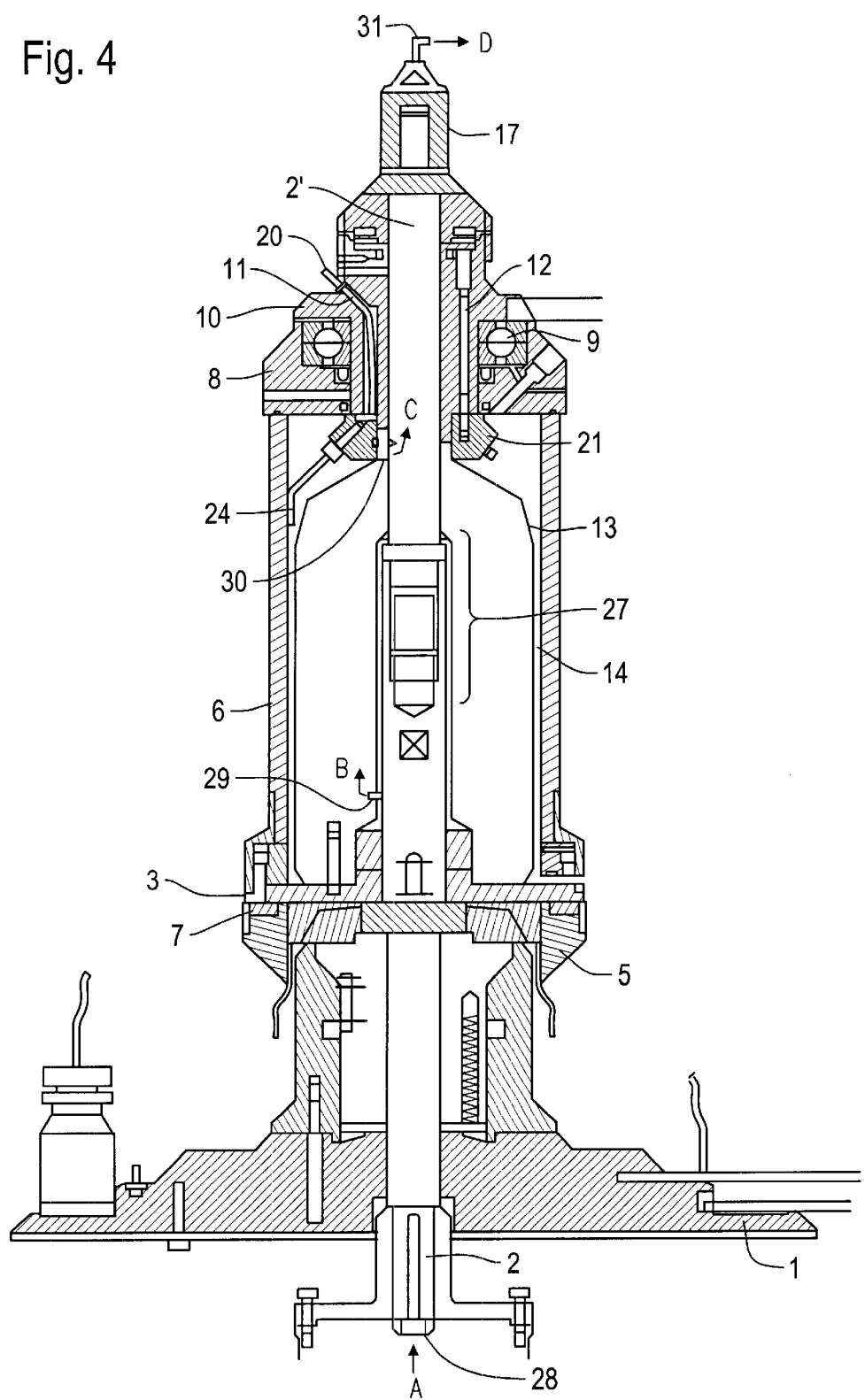

ANNULAR CHROMATOGRAPH

REFERENCE TO RELATED APPLICATIONS

This application is a 371 of PCT/AT99/00075 Mar. 19, 1999.

The invention relates to annular chromatographs comprising a particle bed configured between an inner cylinder and a cylinder sleeve and rotating relative to a stationary base and a stationary feeder head with traversing feeder lines on a rotary plate with eluate drainage lines.

The aim consisted in providing an annular chromatograph design that can be tuned to the problems to be solved, not merely by selection of suitable particle bed material(s) but also by its design, particularly with respect to the height of the particle bed, but also with respect to the particle bed density.

According to the invention, this aim is attained by a modular type block system in which different pairs of inner cylinders and cylinder sleeves, in particular pairs differing in their height, can be shifted relative to each other and/or used together. To this end a central column is provided at the rotary plate onto which all components that must be arranged above the rotary plate are strung as it were.

Accordingly, an annular chromatograph according to the invention is first of all characterized by the fact that at the rotary plate a central column is provided which extends upward and through the feeder head, and on which a tightening device serving to press the feeder head on the cylinder sleeve is arranged.

In preferred embodiments, spacer tubes are present on the tightening device, or else, extension pieces are present on the central column, in order to provide adaptation to cylinder sleeves of different lengths. In either case the annular chromatograph according to the invention can readily be equipped with cylinder sleeves differing in their height.

In another preferred embodiment, cylinder sleeves, preferably with different inner diameters, that can be placed one on top of the other and/or inner cylinder/cylinder sleeve pairs which more particularly are shaped as combination members are provided. In this way several particle beds—superimposed or surrounding each other —can simultaneously be brought into play for the chromatographic separation.

Such combination members preferably contain a fixed particle bed packing, particularly one in the form of a porous matrix obtained by complete polymerization of prepolymer particles in contact with the inner cylinder and cylinder sleeve. Such a preformed matrix is readily cleaned/rinsed after use and can then be reutilized, which leads to an important drop in demand for particle bed material and in the time required for numerous consecutive separations by annular chromatography, since there is no need to recharge the column after each separation while a large number of consecutive separations can be performed as a continuous operation and the annular chromatograph can be refitted extremely rapidly with different particle bed materials.

In preferred annular chromatographs according to the invention, two or more concentric cylinder sleeves with intervening particle beds can be provided while the rotary plate is fitted with matching rows of eluate drainage lines. In this way several separations by annular chromatography can be performed simultaneously in a single installation, and far greater throughputs of the annular chromatograph can be attained.

In a particularly preferred embodiment of the annular chromatograph according to the present invention, the feeder head comprises passages for the feeder lines into which the feeder lines can be inserted and passed through from the interior of the core-sleeve arrangement.

An annular chromatograph according to the invention can additionally comprise a temperature control, for instance by providing heat exchangers for the eluent and/or feed, which in a preferred embodiment are provided in association with the inner cylinder and/or the cylinder sleeve. It thus becomes possible to bring the particle bed to a higher operating temperature for the separation processes or, if necessary, to eliminate any heat liberated by absorption or desorption processes. The heat exchangers used to raise the temperature can be heating devices known as such, those used to lower the temperature can be known coolers functioning as flow-through devices.

BRIEF DESCRIPTION OF THE DRAWINGS

FIG. 1 shows an overall view of an embodiment of an annular chromatograph.

FIGS. 2 and 3 show partial views of two different embodiments of an annular chromatograph.

FIG. 4 shows an overall view of an embodiment of an annular chromatograph.

DESCRIPTION OF THE PREFERRED EMBODIMENTS

A more detailed description of the invention will now be provided with reference to the appended drawings in which FIGS. 1 to 4 all are schematic sectional side elevations. Of these, FIGS. 1 and 4 are overall views and FIGS. 2 and 3 are partial views of annular chromatographs according to the invention, the head design of the annular chromatograph in FIGS. 1 and 2 being different from that in FIGS. 3 and 4.

In FIG. 1 one recognizes a base plate 1 which can for instance be screwed onto a laboratory table, and in which a drive shaft 2 is pivoting. A rotary plate 3 is wedged onto the drive shaft 2 and comprises eluate drainage channels which traverse it along a circular periphery but are not designated in greater detail, while beneath these channels an eluate receiving cup 5 that cannot be rotated is fixed to the bearing bracket 4 for the drive shaft 2, this bracket being formed in one piece with the base plate 1.

Bolted at 7 to the rotary plate 3 is a hollow cylinder 6 which serves as the cylinder sleeve and comprises a retracted roof 8 which in FIG. 1 and FIG. 2 runs parallel to the rotary plate 3 and is connected via a ball bearing 9 to a feed sleeve 10 which during operation does not move relative to the base plate 1 and is traversed by supply channels for feed, eluates, particle bed material, etc. to the interior of the hollow cylinder 6, two of which are designated with 11 and 12.

An inner cylinder 13 is slipped over the drive shaft 2 in the interior of the hollow cylinder 6 and rests on the rotary plate 3 while between the hollow cylinder 6 and the inner cylinder 13 a particle bed space 14 remains in the shape of a cylindrical jacket which is uniformly filled to the desired height with particulate bed material. The inner cylinder 13 has a roof with guide flange 15 which points upward on its upper side away from the rotary plate 3 and holds the roof on the drive shaft 2, and is subject to the action of a helical spring 16 pressing the inner cylinder 13 against the rotary plate 3.

The seat of spring 16 is a tightening sleeve 17 which is counter-screwed to the drive shaft 2 until a pivoting flange 18 of tightening sleeve 17 which supports a ball bearing 19 couples via the free rolling surface of this bearing to the feed sleeve 10. In this way the feed sleeve 10 is supported, both with respect to roof 8 of the hollow cylinder 6 and with respect to the tightening sleeve 17, and can thus readily be held fixed with respect to the rotating parts of the annular chromatograph.

It can be seen when comparing FIGS. 1 and 2 that the height of the particle bed space can be varied with the aid of sets of accessory parts each comprising matched tightening sleeves 17, inner cylinders 13 and hollow cylinders 6. The depth of the particle bed space can likewise be varied by adjusting the diameters of hollow cylinder 6 and inner cylinder 13.

In FIGS. 1 and 2 it can only be seen that supply channels 11 and 12 end at certain points above the inner cylinder 13; in FIG. 3 which also refers to another head design, it is shown by way of example that the supply pipes 20 pass through the supply channels from the interior of the annular chromatograph to the outside. To this end a distribution head 21 which has bores that correspond with the supply channels and contain shoulders to hold an annular flange arranged at the end of the supply pipe 20 is screwed to the feed sleeve 10. Prior to assembly of the chromatograph the supply pipe 20 is pushed upward into the distribution head until its ring flange meets the shoulder of the bore in the distribution head 21; then a sealing nipple 22 is screwed in and a distribution pipe 24 which extends into the annular gap 14 between hollow cylinder 6 and inner cylinder 13 and terminates above the particle bed (not shown) is fastened via a knurled nut 23 at the nipple. Thus, in operation the particle bed is rotating relative to the distribution pipe 24. At the point where supply pipe 20 emerges from the feed sleeve 10, a divided stopper 25 is inserted which merely serves to center the supply pipe 20. Numeral 26 designates a screw serving to vent the interior of the annular chromatograph.

In the design represented in FIG. 3, both the inner cylinder 13 and the hollow cylinder 6 are screwed from below to the rotary plate.

An annular chromatograph design similar to that of FIG. 3 is further shown in FIG. 4, but in this embodiment the drive shaft is made in two pieces, the upper shaft portion 2' with the smaller diameter being pushed into the lower portion 2 and fixed at it in the overlap zone 27 with a screw or catch fastener for instance. The upper shaft portion 2' can be pushed into the lower portion along part of the shaft's full length so that the length of the shaft can be adjusted to match different heights of the cylinder sleeve/inner cylinder pairs 6, 13 and thus different heights of the particle beds.

Additionally the flow path of a flow-through temperature control system provided in this embodiment is marked in FIG. 4. Here the temperature control liquid (that is, a heating or cooling liquid) enters the lower portion of the drive shaft 2 at the intake 28 (arrow A), is conducted within the shaft to the opening 29 where it leaves the shaft and enters the interior of the inner cylinder 13 (arrow B) where it serves to control the temperature of (heat or cool) the particle bed. The flow path continues through outlet 30 where it leaves the interior of the cylinder and reenters the shaft—in this case its upper portion 2' (arrow C)—until the temperature control liquid finally exits from the annular chromatograph at the outlet 31 (arrow D).

Preferably, the temperature control liquid is conducted along a closed circuit, by passing a heat exchanger (not shown) after exiting from 31 and reentering the chromatograph—appropriately heated or cooled—at 28.

The invention has been described with reference to specific embodiments, but it will be understood that those skilled in the art will be able to introduce numerous variations and modifications which are all within the scope of the invention as defined in the associated claims.

What is claimed is:

1. Annular chromatograph comprising a particle bed configured between an inner cylinder and a cylinder sleeve and rotating relative to a stationary base and a stationary feeder head with traversing feeder lines on a rotary plate with eluate drainage lines, characterized in that at the rotary plate (3) a central column (2) is provided which extends upward and through the feeder head (10), and on which a tightening device (16, 17) serving to press the feeder head (10) on the cylinder sleeve (6) is arranged.

2. Annular chromatograph according to claim 1, characterized in that the tightening device (16, 17) comprises spacer tubes (17) in order to be adapted to cylinder sleeves (6) of different lengths.

3. Annular chromatograph according to claim 1, characterized in that the central column (2) comprises extension pieces (2') in order to provide adaptation to cylinder sleeves (6) of different lengths.

4. Annular chromatograph according to claim 1, characterized in that cylinder sleeves (6) are provided that can be placed one on top of the other.

5. Annular chromatograph according to claim 4, characterized in that the cylinder sleeves (6) have different inner diameters.

6. Annular chromatograph according to claim 1, characterized in that inner cylinder/cylinder sleeve pairs (13, 6) are provided.

7. Annular chromatograph according to claim 6, characterized in that the inner cylinder/cylinder sleeve pairs (13, 6) are provided in the form of combination members.

8. Annular chromatograph according to claim 7, characterized in that the combination members contain a fixed particle bed packing.

9. Annular chromatograph according to claim 8, characterized in that the fixed particle bed packing is a porous matrix obtained by complete polymerization of prepolymer particles in contact with the inner cylinder (13) and cylinder sleeve (6).

10. Annular chromatograph according to claim 1, characterized in that two or more concentric cylinder sleeves (6) with intervening particle beds are provided while the rotary plate (3) is fitted with matching rows of eluate drainage lines.

11. Annular chromatograph according to claim 1, characterized in that the feeder head (10) comprises passages (11, 12) for the feeder lines (20) into which the feeder lines (20) can be inserted and passed through from the interior of the core-sleeve arrangement.

12. Annular chromatograph according to claim 1, characterized in that a temperature control is provided.

13. Annular chromatograph according to claim 12, characterized in that heat exchangers are provided for eluents and/or feed.

14. Annular chromatograph according to claim 13, characterized in that the heat exchangers used to raise the temperature are heating devices known as such, and those used to lower the temperature are known flow-through coolers.

15. Annular chromatograph according to claim 12, characterized in that heat exchangers associated with the inner cylinder and/or the cylinder sleeve are provided.

* * * * *